United States Patent
Han et al.

(10) Patent No.: US 9,260,457 B2
(45) Date of Patent: Feb. 16, 2016

(54) LIGAND COMPOUND, A PREPARATION METHOD THEREOF, A TRANSITION METAL COMPOUND INCLUDING THE LIGAND COMPOUND, AND A PREPARATION METHOD THEREOF

(71) Applicant: LG CHEM, LTD., Seoul (KR)

(72) Inventors: Ki Won Han, Daejeon (KR); Seul Ki Kim, Daejeon (KR); Jae Kwon Jang, Daejeon (KR); Hyo Jung Han, Daejeon (KR); Eun Jung Lee, Daejeon (KR); Choong Hoon Lee, Daejeon (KR); In Sung Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/441,418

(22) PCT Filed: Oct. 23, 2013

(86) PCT No.: PCT/KR2013/009468
§ 371 (c)(1),
(2) Date: May 7, 2015

(87) PCT Pub. No.: WO2014/092327
PCT Pub. Date: Jun. 19, 2014

(65) Prior Publication Data
US 2015/0291631 A1    Oct. 15, 2015

(30) Foreign Application Priority Data

Dec. 11, 2012  (KR) .................. 10-2012-0143807
Dec. 11, 2012  (KR) .................. 10-2012-0143808

(51) Int. Cl.
| | | |
|---|---|---|
| C07F 7/00 | (2006.01) |
| C07F 7/02 | (2006.01) |
| C07F 7/08 | (2006.01) |
| C07F 17/00 | (2006.01) |
| C08F 10/06 | (2006.01) |

(52) U.S. Cl.
CPC ............... *C07F 7/0812* (2013.01); *C07F 17/00* (2013.01); *C08F 10/06* (2013.01)

(58) Field of Classification Search
USPC ................................ 546/10, 14; 548/402, 406
See application file for complete search history.

(56) References Cited

U.S. PATENT DOCUMENTS

| | | |
|---|---|---|
| 5,064,802 A | 11/1991 | Stevens et al. |
| 5,905,162 A | 5/1999 | Lin |
| 7,053,160 B1 | 5/2006 | Bingel et al. |
| 8,207,281 B2 | 6/2012 | Chevalier |
| 2009/0186995 A1 | 7/2009 | Canich et al. |
| 2011/0152529 A1 | 6/2011 | Lee et al. |

FOREIGN PATENT DOCUMENTS

| | | |
|---|---|---|
| EP | 1 462 464 A1 | 9/2004 |
| EP | 2103634 A1 | 9/2009 |
| KR | 10-2001-0101034 A | 11/2001 |
| KR | 10-2005-0085300 A | 8/2005 |
| KR | 10-0820542 B1 | 4/2008 |
| KR | 10-2008-0065868 A | 7/2008 |
| KR | 10-0986301 B1 | 10/2010 |
| KR | 10-0999592 B1 | 12/2010 |
| WO | WO 2005/058929 A1 | 6/2005 |
| WO | WO 2012/084961 A1 | 6/2012 |

OTHER PUBLICATIONS

Beswick, C.L. et al, "Metal-Alkyl Group Effects on the Thermodynamic Stability and Stereochemical Mobility of B(C6F5)3-Derived Zr and Hr," J. Am. Chem. Soc., 2000, vol. 122, pp. 10358-10370.
International Search Report and Written Opinion of the International Searching Authority dated Jan. 28, 2014 for Appl. No. PCT/KR2013/009468 (w/ English translation).
Nifant'ev, I.E. et al., "Novel Effective Racemoselective Method for the Synthesis of ansa-Zirconocenes and Its Use for the Preparation of C2-Symmetric Complexes Based on 2-Methyl-4-aryltetrahydro(s)indacene as Catalysts for Isotactic Propylene Polymerization and Ethylene-Propylene Copolymerization," Organometallics 2012 vol. 31 pp. 4340-4348.

*Primary Examiner* — Charanjit Aulakh
(74) *Attorney, Agent, or Firm* — Birch, Stewart, Kolasch & Birch, LLP

(57) ABSTRACT

The present invention relates to a novel ligand compound, a preparation method thereof, a transition metal compound including the ligand compound, and a preparation method thereof. The ligand compound of novel structure according to the present invention and the transition metal compound including the same may be used as a polymerization reaction catalyst for preparing olefin polymers.

12 Claims, No Drawings

LIGAND COMPOUND, A PREPARATION METHOD THEREOF, A TRANSITION METAL COMPOUND INCLUDING THE LIGAND COMPOUND, AND A PREPARATION METHOD THEREOF

BACKGROUND OF THE INVENTION (a) Field of the Invention

The present invention relates to a novel ligand compound, a preparation method thereof, a transition metal compound including the ligand compound, and a preparation method thereof. This application claims the benefit of Korean Patent Application No. 10-2012-0143807, filed in the Korean Intellectual Property Office on Dec. 11, 2012, Korean Patent Application No. 10-2012-0143808, filed in the Korean Intellectual Property Office on Dec. 11, 2012, which are all hereby incorporated by reference in their entireties into this application.

(b) Description of the Related Art

For a long time, there have been many advances in metallocene catalyst for olefin polymerization. Metallocene compounds are generally activated by an aluminoxane, a borane, a borate, or other activators to be used. For example, a metallocene compound having a ligand including cyclopentadienyl group and two sigma chloride ligands uses an aluminoxane as an activator. It was reported that the activity of the catalyst may increase when the chloride group of such metallocene compound is substituted with other ligands (for example, benzyl group or trimethylsilylmethyl group ($-CH_2SiMe_3$)).

European Patent No. 1462464 discloses a polymerization example using a hafnium metallocene compound including chloride, benzyl, and trimethylsilylmethyl groups. In addition, it was reported that the generation energy of activated species may vary according to the alkyl ligand combined to the center metal (J. Am. Chem. Soc. 2000, 122, 10358). Korean Patent No. 820542 discloses a catalyst for olefin polymerization having a quinoline-based ligand, and this patent relates to a catalyst having a leaving group including silicone or germanium atom in addition to methyl group.

Dow Co. had presented [$Me_2Si(Me_4C_5)NtBu$]$TiCl_2$ (Constrained-Geometry Catalyst, hereinafter 'CGC') in the early 1990's (U.S. Pat. No. 5,064,802), the superior aspects of the CGC to prior known metallocene catalysts in copolymerization reaction of ethylene and α-olefin can be largely summarized into two ways as follows: (1) it shows high activity even in high polymerization temperature and forms a polymer of high molecular weight, (2) the copolymerizing ability of α-olefin such as 1-hexene and 1-octene which have large steric hindrance is also very excellent. As various characteristics in the polymerization reaction of the CGC became gradually known, there have been many efforts to synthesize derivatives of the same for using it as a polymerization catalyst in the academic world and the industrial world.

As an approaching method, a synthesis of a metal compound to which various bridges and nitrogen substituents are introduced instead of silicone bridges and a polymerization using the same have been attempted. Representative metal compounds known up to recently include phosphorus, ethylene or propylene, methylidene, and methylene bridges respectively introduced thereto instead of silicone bridge of CGC structure, but they didn't show excellent results in the aspects of polymerization activity or copolymerization performance in comparison to CGC when they were applied to polymerization of ethylene or copolymerization of ethylene and alpha olefins.

As other approaching method, compounds including oxido ligands instead of amido ligands of the CGC have been largely synthesized and polymerizations using the same have been partially attempted.

However, very few catalysts have been being applied in practice in commercial factories among above attempts.

SUMMARY OF THE INVENTION

It is an aspect of the present invention to provide a novel ligand compound and a preparation method thereof for resolving the problems.

It is another aspect of the present invention to provide a transition metal compound including the ligand compound and a preparation method thereof.

In order to achieve the goals, the present invention provides the ligand compound represented by the following Chemical Formula 1:

[Chemical Formula 1]

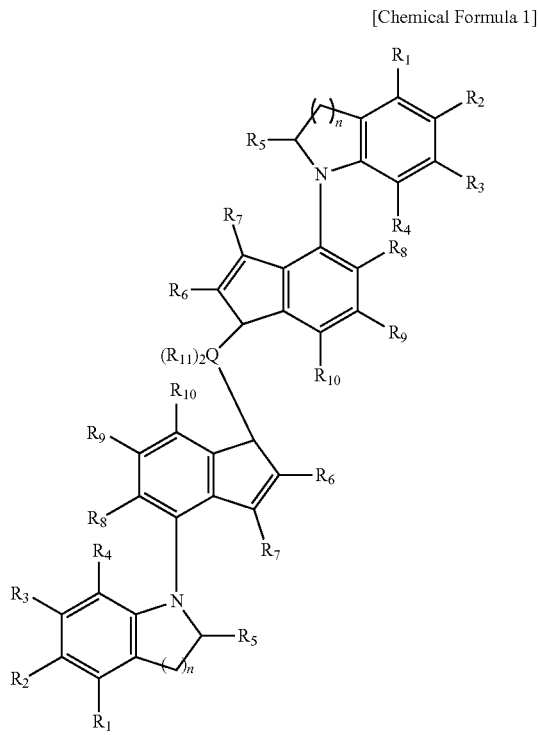

In Chemical Formula 1, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl; and Q is carbon or silicon.

Furthermore, the present invention provides a preparation method of the ligand compound represented by Chemical Formula 1 including the steps of:

carrying out the reaction of the compound represented by the following Chemical Formula 3 and the compound represented by the following Chemical Formula 4 so as to prepare the compound represented by the following Chemical Formula 5; and carrying out the reaction of the compound represented by the following Chemical Formula 5 or the lithium salt thereof and the compound represented by the following Chemical Formula 6:

[Chemical Formula 3]

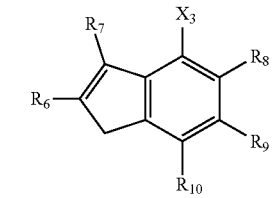

[Chemical Formula 4]

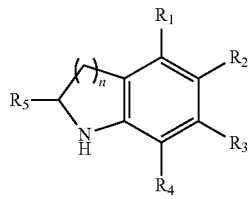

[Chemical Formula 5]

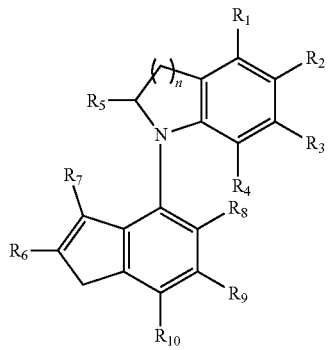

[Chemical Formula 6]

$(R_{11})_2QCl_2$

[Chemical Formula 1]

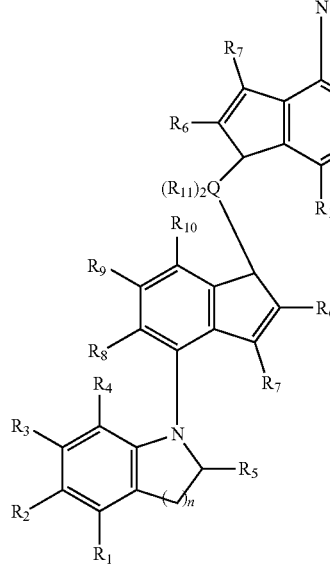

In Chemical Formulae 1, 3, 4, 5, and 6, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

$X_3$ is a halogen; and

Q is carbon or silicon.

Furthermore, the present invention provides the transition metal compound represented by the following Chemical Formula 2:

[Chemical Formula 2]

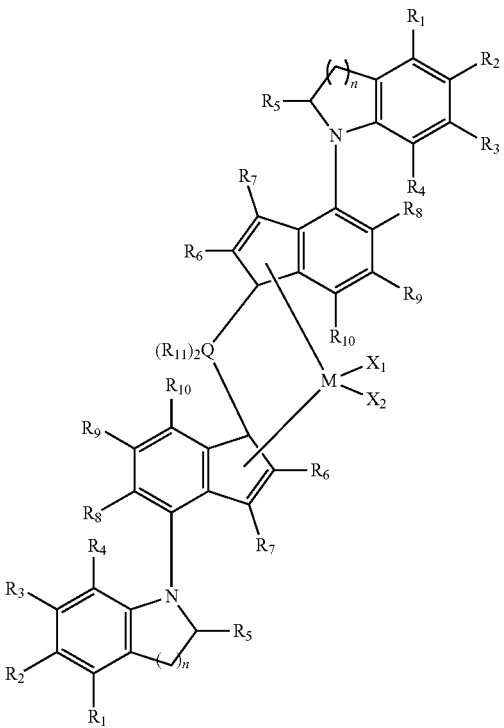

In Chemical Formula 2, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

Furthermore, the present invention provides a preparation method of the transition metal compound represented by the following Chemical Formula 2 including the step of carrying out the reaction of the ligand compound represented by the following Chemical Formula 1 and the compound represented by the following Chemical Formula 7.

[Chemical Formula 1]

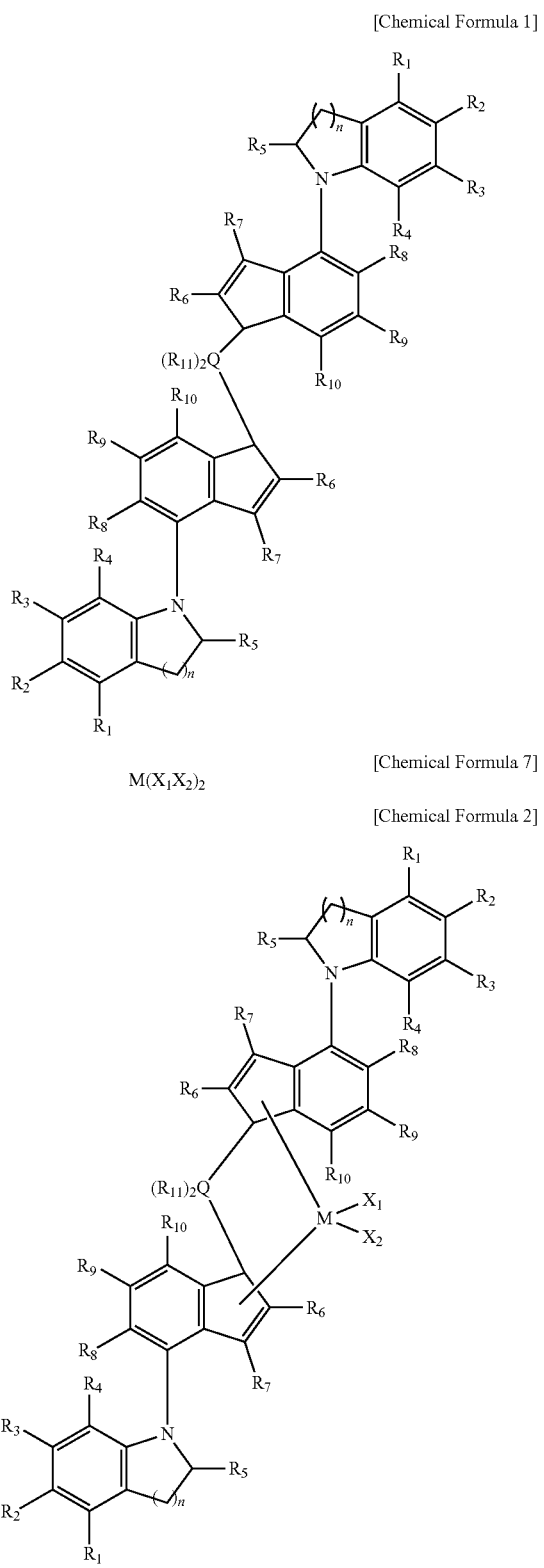

M(X₁X₂)₂ [Chemical Formula 7]

[Chemical Formula 2]

In Chemical Formulae 1, 2, and 7, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

The novel ligand compound of the present invention and the transition metal compound including the same may be usefully used as a catalyst for a polymerization reaction in the preparation of an olefin-based polymer.

DETAILED DESCRIPTION OF THE EMBODIMENTS

The terms used in this description are just for explaining exemplary examples and it is not intended to restrict the present invention. The singular expression may include the plural expression unless it is differently expressed contextually. It must be understood that the terms such as "include", "equip", and "have" in the present description are only used for designating the existence of characteristics taken effect, numbers, steps, components, or combinations thereof, and do not exclude the existence or the possibility of addition of one or more different characteristics, numbers, steps, components of combinations thereof beforehand.

The present invention can be variously modified and have various examples, and specific examples of the present invention are explained in this description. However, it is not intended to limit the present invention to the specific examples and it must be understood that the present invention includes every modifications, equivalents, or replacements included in the idea and technical scope of the present invention.

Hereinafter, the present invention is explained in more detail.

According to one aspect of the present invention, the ligand compound represented by the following Chemical Formula 1 is provided.

[Chemical Formula 1]

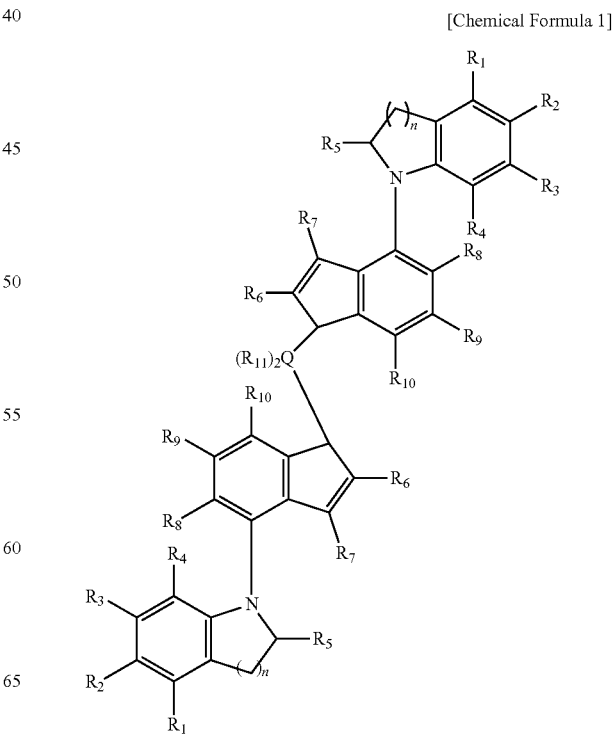

In Chemical Formula 1, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl; and Q is carbon or silicon.

Details of each substituent defined in Chemical Formula 1 are as follows.

The alkyl includes a linear or branched alkyl group.

The alkenyl includes a linear or branched alkenyl group.

According to one embodiment of the present invention, the aryl is preferably a $C_6$-$C_{20}$ aryl group and, specifically, it may be phenyl, naphthyl, anthracenyl, pyridyl, dimethylanilinyl, anisolyl, and so on, but it is not limited to or by them.

The alkylaryl means an aryl group substituted with the alkyl group.

The arylalkyl means an alkyl group substituted with the aryl group.

The halogen means fluorine, chlorine, bromine, or iodine.

The alkylamino means an amino group substituted with the alkyl group and, specifically; it may be dimethylamino, diethylamino, and so on, but it is not limited to or by them.

The arylamino means an amino group substituted with the aryl group and, specifically, it may be phenylamino and so on, but it is not limited to or by them.

The silyl may be trimethylsilyl, triethylsilyl, tripropylsilyl, tributylsilyl, trihexylsilyl, triisopropylsilyl, triisobutylsilyl, triethoxysilyl, triphenylsilyl, tris(trimethylsilyl)silyl, and so on, but it is not limited to or by them.

The aryl is preferably a $C_6$-$C_{20}$ aryl group and, specifically, may be phenyl, naphthyl, anthracenyl, pyridyl, dimethylanilinyl, anisolyl, and so on, but it is not limited to or by them.

The ligand compound represented by Chemical Formula 1 may be represented by any one of the following structural formulae but it is not limited to or by them.

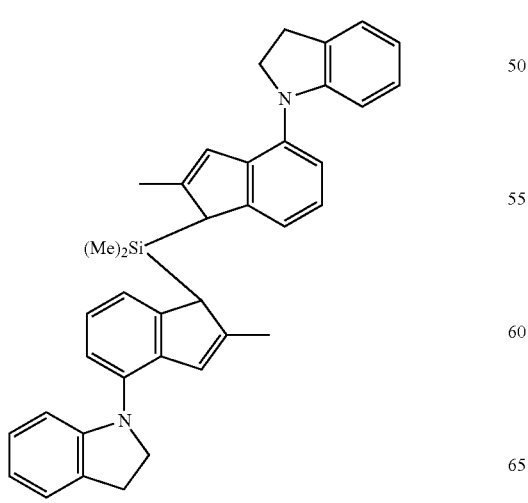

-continued

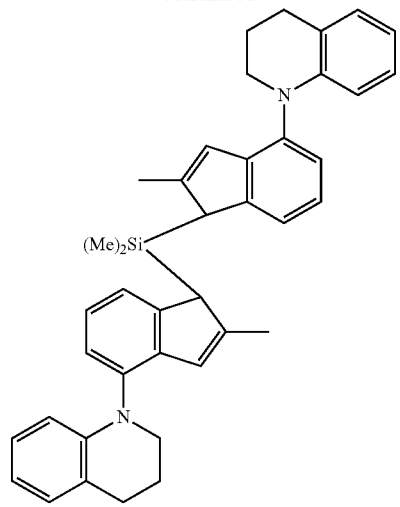

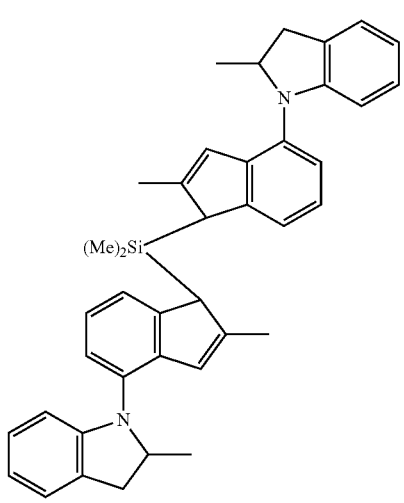

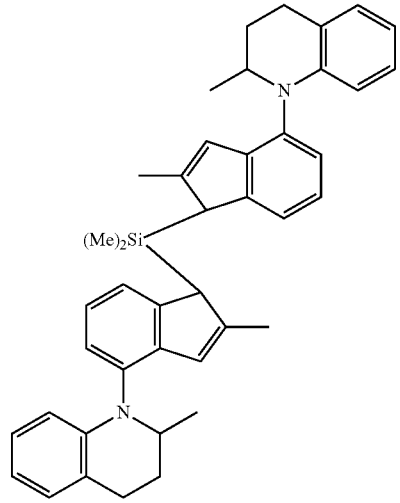

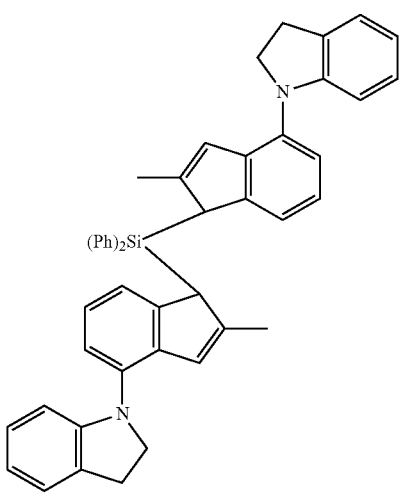

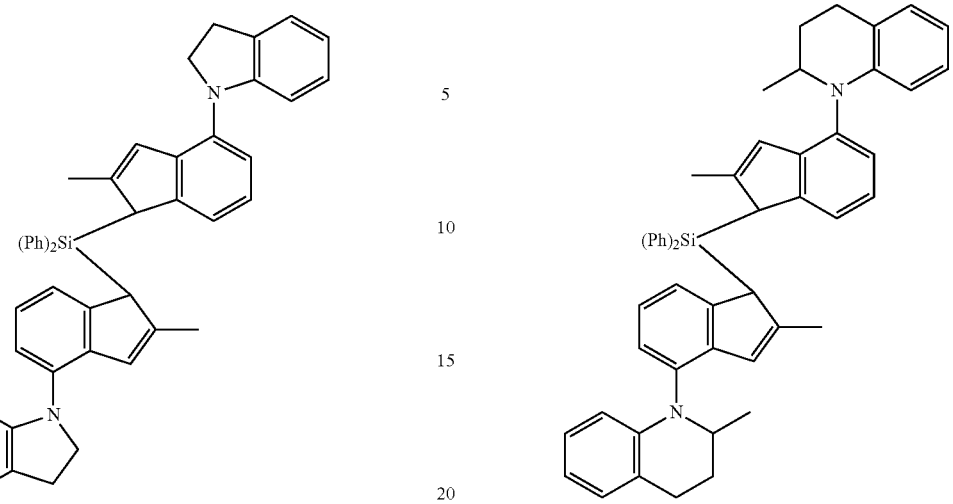

In the structural formulae, Me means methyl group and Ph means phenyl group.

The compound represented by Chemical Formula 1 may be a ligand compound which can form a chelate with a metal.

Furthermore, according to another aspect of the present invention, a preparation method of the ligand compound represented by the following Chemical Formula 1 including the steps of carrying out the reaction of the compound represented by the following Chemical Formula 3 and the compound represented by the following Chemical Formula 4 so as to prepare the compound represented by the following Chemical Formula 5; and carrying out the reaction of the compound represented by the following Chemical Formula 5 or the lithium salt thereof and the compound represented by the following Chemical Formula 6 is provided.

[Chemical Formula 3]

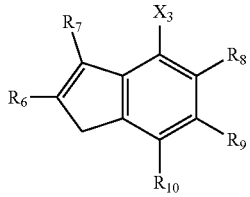

[Chemical Formula 4]

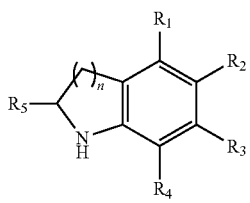

[Chemical Formula 5]

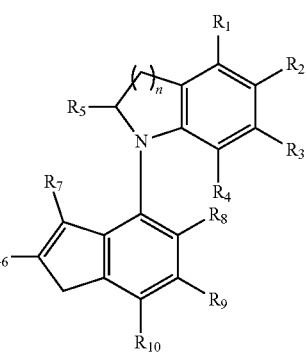

-continued

[Chemical Formula 6]

$(R_{11})_2QCl_2$

[Chemical Formula 1]

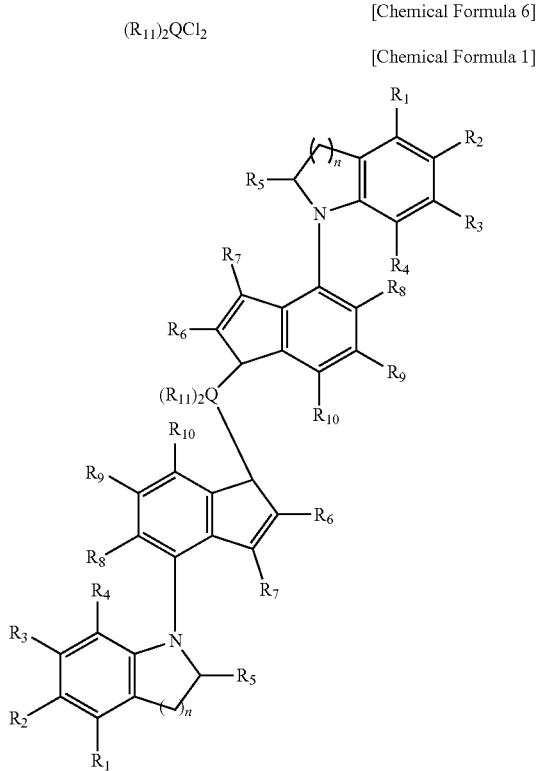

In Chemical Formulae 1, 3, 4, 5, and 6, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

$X_3$ is a halogen; and

Q is carbon or silicon.

In the preparation method of the ligand compound, at first, the compound represented by Chemical Formula 5 is prepared by the reaction of the compound represented by Chemical Formula 3 and the compound represented by Chemical Formula 4.

More specifically, according to one embodiment of the present invention, the compound represented by Chemical Formula 5 may be prepared by carrying out the coupling reaction of the indenyl halide compound represented by Chemical Formula 3 and the derivative compound of indoline or tetrahydroquinoline represented by Chemical Formula 4 in the presence of a base or a palladium catalyst to form C—N bond. At this time, the palladium catalyst is not limited particularly and, for example, it may be bis(tri(tert-butyl)phosphine))palladium (((tert-Bu)$_3$P)$_2$Pd), tetrakis(triphenylphosphine)palladium (Pd(PPh$_3$)$_4$), palladium chloride (PdCl$_2$), palladium acetate (Pd(OAc)$_2$), bis(dibenzylideneacetone) palladium (Pd(dba)$_2$), and the like.

Subsequently, the ligand compound represented by Chemical Formula 1 can be obtained by carrying out the reaction of the compound represented by Chemical Formula 5 or the lithium salt thereof and the compound represented by Chemical Formula 6.

More specifically, according to one embodiment of the present invention, the lithium salt of the compound represented by Chemical Formula 5 is prepared by the reaction of the compound represented by Chemical Formula 5 and an organic lithium compound such as n-BuLi. Subsequently, the lithium salt is mixed with the compound represented by Chemical Formula 6 and the mixture is stirred to react. The reaction product is filtered and the precipitate is obtained. And then, the precipitate is washed and dried under decompression, and the ligand compound represented by Chemical Formula 1 having the structure in which the derivatives of indenyl group are C2-asymmetrically crosslinked by Q (carbon or silicon) can be obtained According to the preparation method of the present invention, the ligand compound may be obtained as any one form of racemic body or meso compound, or a mixture of the racemic body and the meso compound.

Furthermore, according to another aspect of the present invention, the transition metal compound represented by the following Chemical Formula 2 is provided.

The transition metal compound of the present invention has the structure in which a Group 4 transition metal is combined with the ligand compound represented by Chemical Formula 1 by coordinate bond, and it may be represented by the following Chemical Formula 2.

[Chemical Formula 2]

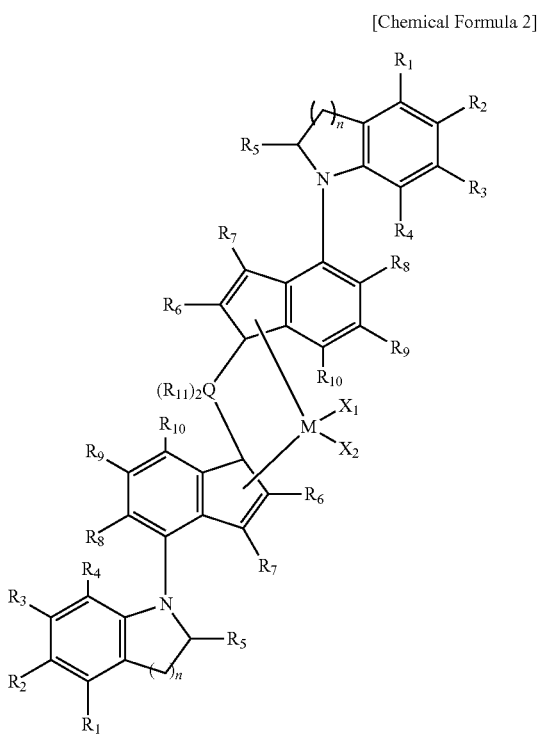

In Chemical Formula 2, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

According to one embodiment of the present invention, the Group 4 transition metal corresponding to M may be Ti, Zr, Hf, and so on but it is not limited to or by them.

Furthermore, according to one embodiment of the present invention, the transition metal compound represented by Chemical Formula 2 may be represented by any one of the following structural formulae but it is not limited to or by them.

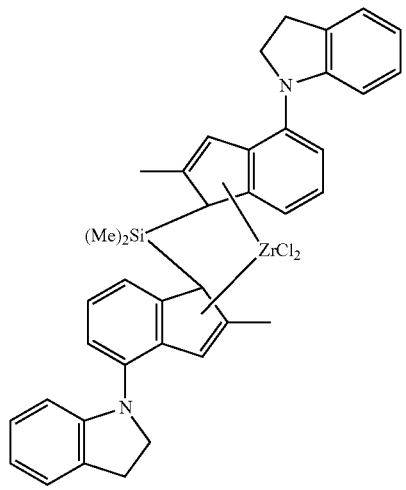

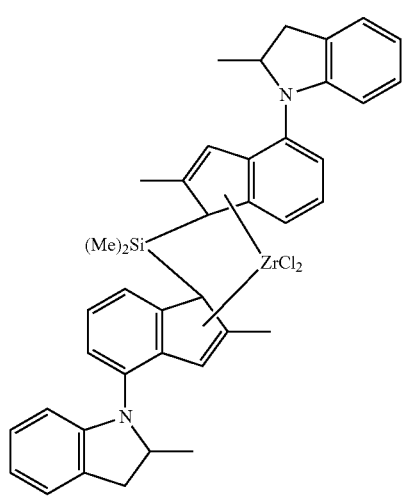

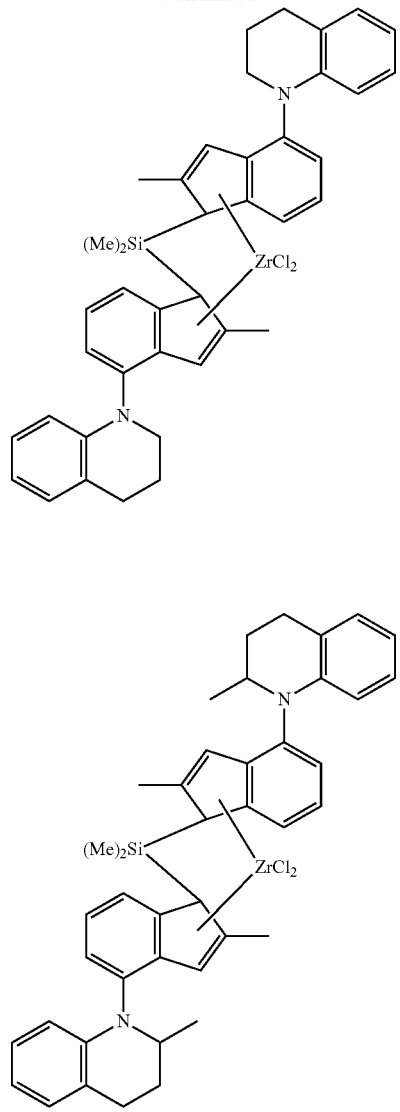

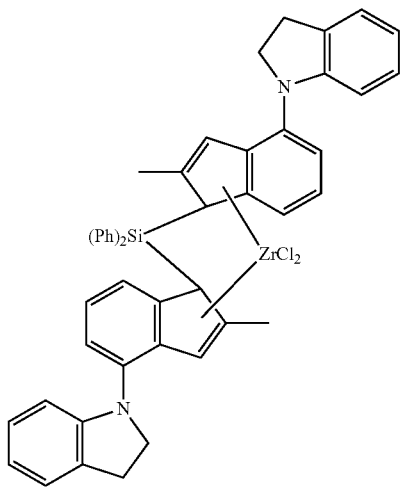

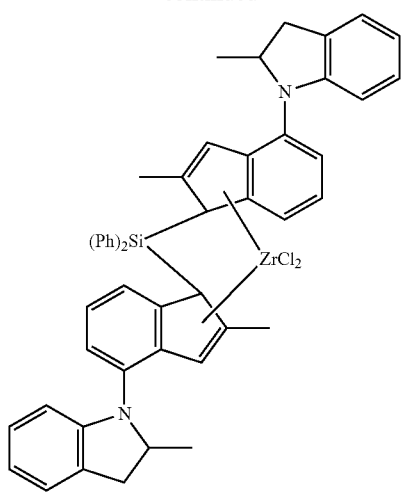
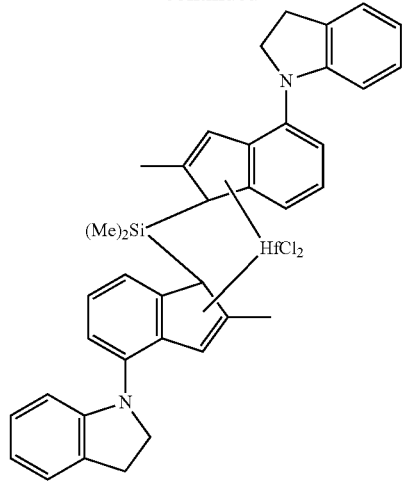
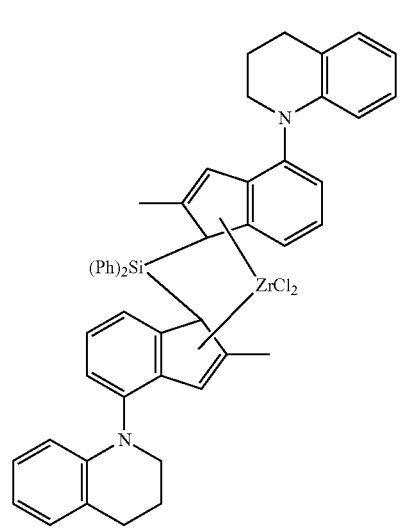
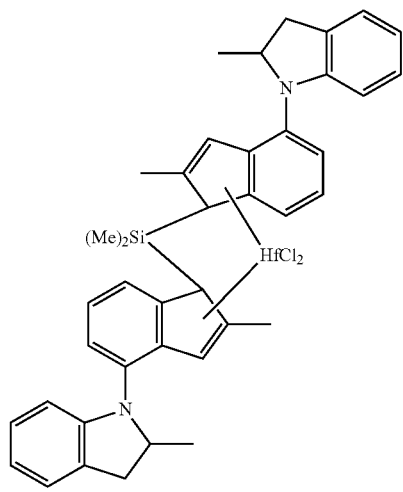
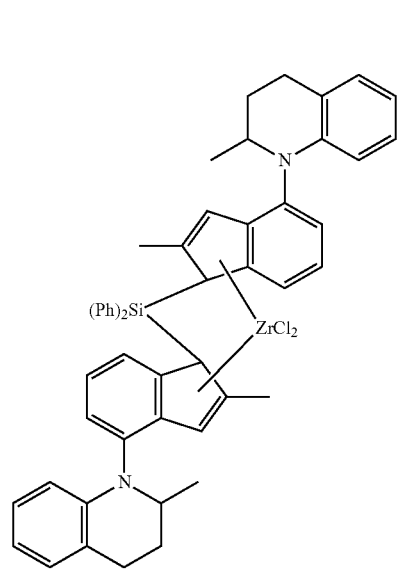
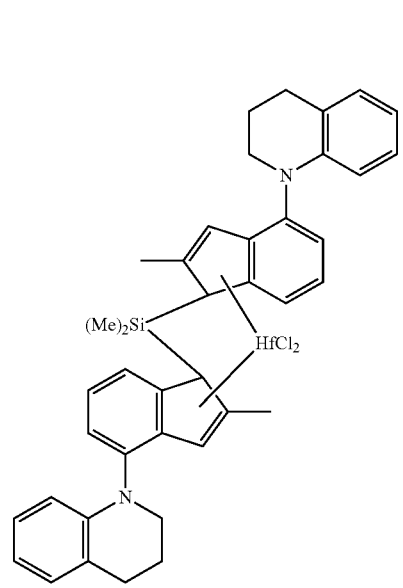

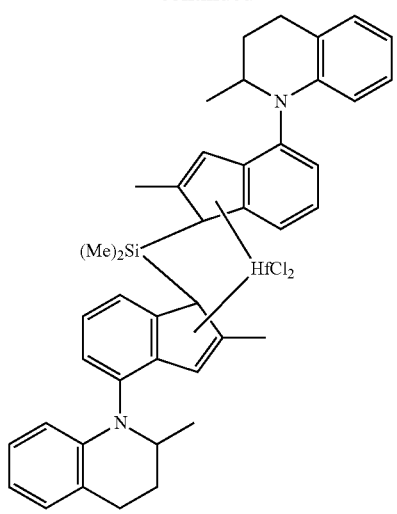

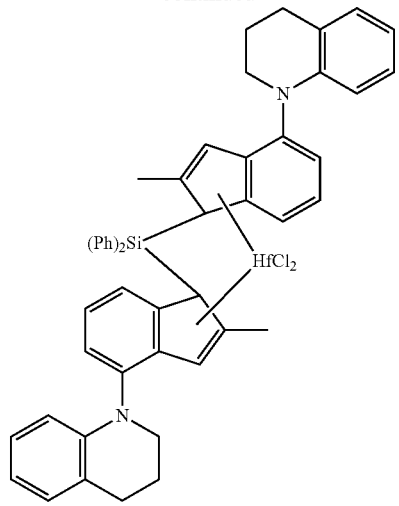

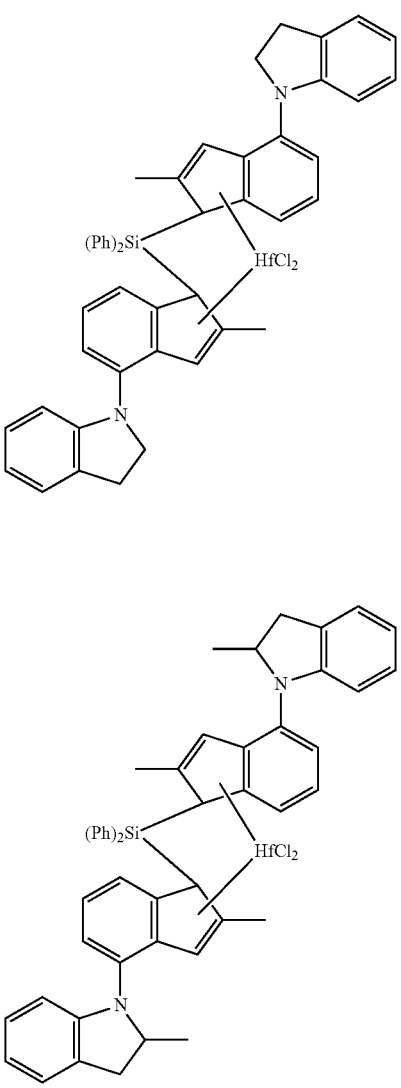

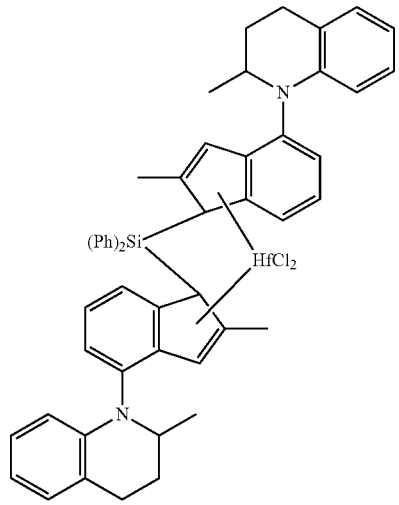

In the structural formulae, Me means methyl group and Ph means phenyl group.

Furthermore, according to another aspect of the present invention, a preparation method of the transition metal compound represented by Chemical Formula 2 is provided.

The preparation method of the transition metal compound according to another aspect of the present invention includes the step of carrying out the reaction of the ligand compound represented by the following Chemical Formula 1 and the compound represented by the following Chemical Formula 7.

[Chemical Formula 1]

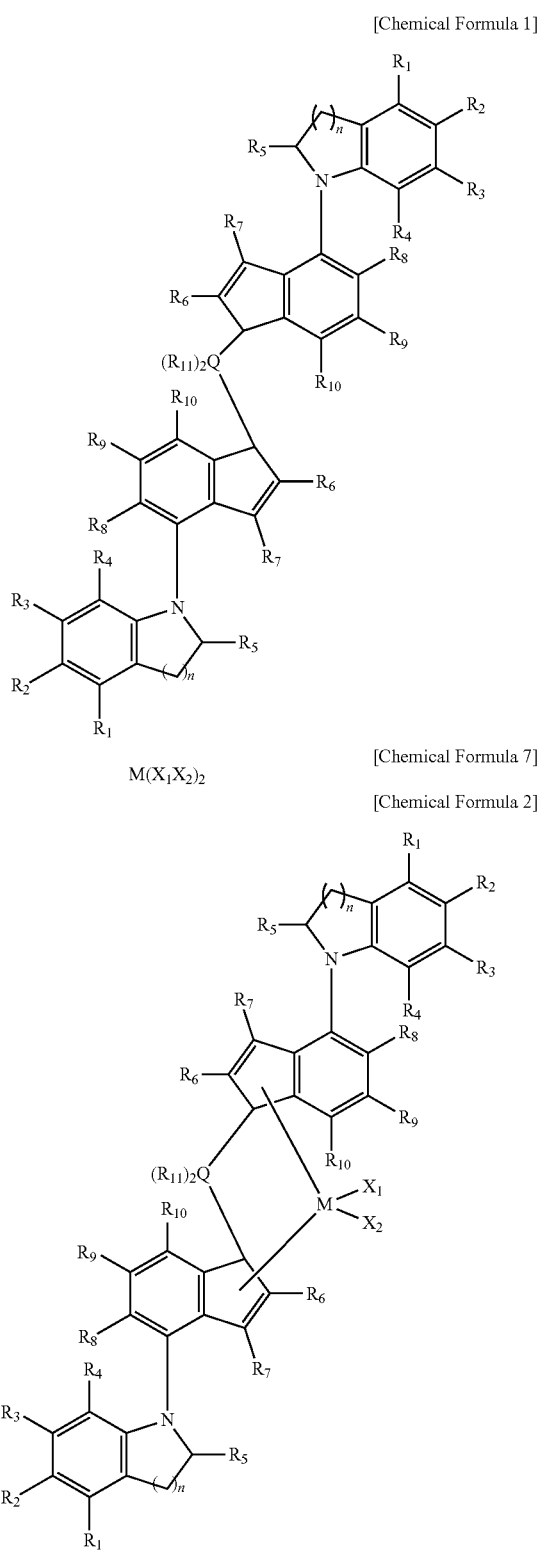

[Chemical Formula 7]

M(X₁X₂)₂

[Chemical Formula 2]

In Chemical Formulae 1, 2, and 7, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

According to one embodiment of the present invention, the Group 4 transition metal corresponding to M may be Ti, Zr, Hf, and so on but it is not limited to or by them.

More specifically, at first, the ligand compound represented by Chemical Formula 1 is made into the lithium salt thereof by the reaction with an organic lithium compound such as n-BuLi. The lithium salt is mixed with the metal source represented by Chemical Formula 7 and the mixture is stirred to react. The reaction product is filtered and the precipitate is obtained. And then, the organic metal compound represented by Chemical Formula 2 having the complex form in which a metal atom is combined with the ligand compound is obtained by washing the precipitate and drying the same under decompression.

According to the preparation method of the present invention, the transition metal compound represented by Chemical Formula 2 may be obtained respectively as any one of racemic body or meso compound, or a mixture of the racemic body and the meso compound. When the compound is a mixture of the racemic body and the meso compound, it is possible to obtain only the racemic body of the transition metal compound finally through a recrystallization step.

The ligand compound represented by Chemical Formula 1 and the transition metal compound represented by Chemical Formula 2 have a structure in which bisindenyl groups are crosslinked by carbon or silicon, and each indenyl group is connected to indoline group or tetrahydroquinoline group so as to show C2-asymmetric crosslinking structure. Since the transition metal compound of the present invention includes indoline group or tetrahydroquinoline group which is plenty of electrons as disclosed above, electron density of the center metal of the same increases, the stability at high temperature thereof is high, and it can be usefully used to synthesize polyolefin polymers of high molecular weight, particularly, isotatic polyolefin polymers, for example, isotatic polypropylene.

The ligand compound of novel structure according to the present invention and the transition metal compound including the same may be used as a polymerization reaction catalyst for preparing olefin polymers.

Hereinafter, preferable examples and comparative examples are presented for understanding the present invention. However, the following examples are only for illustrating the present invention and the present invention is not limited to or by them.

EXAMPLES

In the following Examples, term "overnight" or "through the night" means about 12 to 16 hrs and term "room temperature" means the temperature of about 20 to 30° C. Organic reagents and solvents were purchased from Aldrich Co., Ltd. and Merck Co., Ltd. and refined by a standard method before use. In every steps of the syntheses, contact with air or moisture was cut off for increasing repeatability of experimental.

NMR spectrum was obtained by using a 500 MHz NMR spectrometer for confirming the structure of the produced compound.

Synthesis of Ligand Compound and Transition Metal Compound

Example 1

Synthesis of 1-(2-methyl-1H-inden-4-yl)-1,2,3,4-tetrahydroquinole

After putting 4-bromo-2-methyl-1H-indene (15.7 g, 75.63 mmol), 1,2,3,4-tetrahydroquinone (11.08 g, 83.19 mmol), LiOtBu (18.16 g, 226.89 mmol), and Pd(P(tBu)$_3$)$_2$ (0.77 g, 1.5 mmol) in a 500 mL 2-neck Schlenk flask and dissolving the starting material by adding 252 mL of dry toluene thereto, the mixture was stirred through the night in an oil bath of 110° C. After cooling the mixture to room temperature, the reaction was terminated by adding 151 ml of deionized water.

After separating the organic layer therefrom, the water layer was extracted twice with 50 mL of dichloromethane (DCM). The collected organic layer was dried with Na$_2$SO$_4$ and filtered and distilled. And then, the compound of orange color (15.8 g, quantitative yield compared to 4-bromo-2-methyl-1H-indene, 80% yield compared to the starting material) was obtained by vacuum drying the distilled compound at 60° C. through the night.

$^1$H-NMR (CDCl$_3$): δ 7.30-7.20 (m, 3H in isomers), 7.15-7.10 (d, J=7.5 Hz, 2H in isomers), 7.15-7.10 (d, J=8.0 Hz, 1H in isomers), 7.10-7.05 (d, J=8.0 Hz, 111 in isomers), 7.05-7.00 (d, J=7.5 Hz, 3H in isomers), 7.00-6.95 (d, J=7.5 Hz, 2H in isomers), 6.90-6.80 (t, J=7.5 Hz, 3H in isomers), 6.65-6.58 (m, 3H in isomers), 6.48 (s, 2H in isomers), 6.33 (s, 1H in isomers), 6.30-6.25 (d, J=8.0 Hz, 1H in isomers), 6.25-6.22 (d, J=8.0 Hz, 2H in isomers), 3.62-3.59 (t, J=5.5 Hz, 6H in 2-quinolinyl of isomers), 3.33 (s, 2H in 1H-indene of isomers), 3.10 (s, 3H in 1H-indene of isomers), 3.00-2.85 (m, 6H in 4-quinolinyl of isomers), 2.22-2.00 (m, 14H in 3H-quinolinyl and 2-Me of isomers)

Synthesis of bis(4-(3,4-dihydroquinolin-1(2H)-yl)-2-methyl-1H-inden-1-yl)-dimethyl silane After putting 1-(2-methyl-1H-inden-4-yl)-1,2,3,4-tetrahydroquinole (15.8 g, 60.5 mmol) in a 500 mL Schlenk flask and dissolving the starting material by adding 300 mL of dry diethyl ether thereto, n-BuLi (2.5 M in n-Hx) (26.6 mL) was added thereto at −78° C. and the mixture was stirred at room temperature through the night. And then, the mixture was filtered by using a glass frit (G4). The remaining solid on the glass frit was vacuum dried and the lithiated product (14.4 g, 89% yield) of white solid was obtained. The lithiated product (14.2 g, 53.1 mmol) was put in a 500 mL Schlenk flask in a glove box and 152 mL of dry toluene and 7.6 mL of THF were added thereto for dissolving the same. After lowering the temperature to −30° C., Me$_2$SiCl$_2$ (3.2 mL, 26.6 mmol) was added thereto and the mixture was stirred at room temperature for a day. And then, the mixture was stirred for 5 hrs in an oil bath of 140° C. After cooling the same to room temperature, the reaction was terminated by adding 50 ml of deionized water.

After separating the organic layer therefrom, the water layer was extracted twice with 50 mL of dichloromethane (DCM). The collected organic layer was dried with K$_2$CO$_3$ and filtered and distilled. And then, the ligand compound of brownish white solid (15.8 g, quantitative yield compared to lithiated product, 89% yield compared to the starting material) was obtained by vacuum drying the distilled compound at 60° C. through the night. As the result of $^1$H-NMR analysis, the ratio of rac:meso was about 1:1.

$^1$H-NMR (CDCl$_3$): δ 7.40 (d, J=7.5 Hz, 2H, 7,7'-H in indenyl of rac-isomer), 7.25 (d, J=7.5 Hz, 2H, 7,7'-H in indenyl of meso-isomer), 7.15 (t, J=7.5 Hz, 2H, 6,6'-H in indenyl of rac-isomer), 7.12 (t, J=8.0 Hz, 2H, 6,6'-H in indenyl of meso-isomer), 7.10 (d, J=7.5 Hz, 2H, 5,5'-H in quinolinyl of rac-isomer), 7.08 (d, J=7.5 Hz, 2H, 5,5'-H in quinolinyl of meso-isomer), 7.02 (dd, J$_1$=7.0 Hz, J$_2$=1.0 Hz, 4H, 5,5'-H in indenyl of rac- and meso-isomers), 6.85-6.81 (m, 4H, 7,7'-H in quinolinyl of rac- and meso-isomers), 6.60 (td, J$_1$=7.5 Hz, J$_2$=1.0 Hz, 4H, 6,6'-H in quinolinyl of rac- and meso-isomers), 6.46 (s, 4H, 3,3'-H in indenyl of rac- and meso-isomers), 6.26 (d, J=8.0 Hz, 4H, 8,8'-H in quinolinyl of rac- and meso-isomers), 3.81 (s, 2H, 1,1'-H in indenyl of rac-isomer), 3.79 (s, 2H, 1,1'-H in indenyl of meso-isomer), 3.69-3.57 (m, 8H, 2,2'-H in quinolinyl of rac- and meso-isomers), 2.92 (t, J=6.0 Hz, 8H, 4,4'-H in quinolinyl of rac- and meso-isomers), 2.21 (d, J=0.5 Hz, 6H, 2,2'-Me in meso-isomer), 2.13 (d, J=1.0 Hz, 6H, 2,2'-Me in rac-isomer), 2.13-2.08 (m, 8H, 3,3'-H in quinolinyl of rac- and meso-isomers), −0.27 (s, 3H, SiMe of meso-isomer), −0.29 (s, 6H, SiMe$_2$ of rac-isomer), −0.30 (s, 3H, SiMe' of meso-isomer)

Synthesis of rac-dimethylsilylene-bis(4-(3,4-dihydroquinolin-1(2H)-yl)-2-methyl-indenyl) zirconium dichloride After putting 10.4 g of bis(4-(3,4-dihydroquinolin-1(2H)-yl)-2-methyl-1H-inden-1-yl)-dimethyl silane (18 mmol, rac:meso=1:1) in a 500 mL Schlenk flask and dissolving the starting material by adding 285 mL of dry toluene thereto, 14.4 mL of n-BuLi (2.5 M in n-Hx) was added thereto at −78° C. and the mixture was stirred at room temperature for 5 hrs. The mixture was cooled to −78° C. again and transferred to a Schlenk flask in which 4.2 g of ZrCl$_4$ solution (18 mmol in 60 mL toluene) of −78° C. was put beforehand by using a cannula, and then it was stirred at room temperature through the night. After the reaction was terminated, the product was filtered with a glass frit (G4) on which celite spread. The remaining solid on the glass frit was washed out thrice with about 5 mL of dry toluene. The toluene solution was vacuum dried and the solid of red color was obtained. The remaining solid on the glass frit was dissolved out by using dichloromethane (DCM). The solid of red color was obtained by vacuum drying the DCM filtrate. As the result of $^1$H-NMR analysis, both of two solids were Zr complex of rac:meso=1:1. After collecting the crude product and storing the same in the oil bath of 45° C., 50 mL of dry toluene was added thereto with stirring for dissolving the same. The solution was stored in a freezer of −30° C. for 3 days for recrystallization. The obtained red solid was filtered with a glass frit (G4) and washed twice with 5 mL of dry n-hexane, and then 1.3 g of the final product (1.9 mmol, 10.4% yield) of racemic body was obtained by vacuum drying the solid.

$^1$H-NMR (Tol-d$_3$): δ 7.19 (d, J=8.5 Hz, 2H, 7,7'-H in indenyl), 7.02 (d, J=7.5 Hz, 2H, 5,5'-H in quinolinyl), 6.92 (d, J=7.5 Hz, 2H, 5,5'-H in indenyl), 6.85-6.82 (m, 2H, 7,7'-H in quinolinyl), 6.76 (dd, J$_1$=8.5 Hz, J$_2$=7.5 Hz, 2H, 6,6'-H in indenyl), 6.70-6.68 (m, 2H, 6,6'-H in quinolinyl), 6.67 (s, 2H, 3,3'-H in indenyl), 6.54 (d, J=8.5 Hz, 2H, 8,8'-H in quinolinyl), 3.85-3.69 (m, 4H, 2,2'-H in quinolinyl), 2.65-2.54 (m, 4H, 4,4'-H in quinolinyl), 1.95 (s, 6H, 2,2'-Me), 1.90-1.70 (m, 4H, 3,3'-H in quinolinyl), 0.84 (s, 6H, SiMe$_2$)

Example 2

Synthesis of rac-dimethylsilylene-bis(4-(3,4-dihydroquinolin-1(2H)-yl)-2-methyl-indenyl) hafnium dichloride After putting 3 g of bis(4-(3,4-dihydroquinolin-1(2H)-yl)-2-methyl-1H-inden-1-yl)-dimethyl silane of Example 1 (5.2 mmol, rac:meso=1:1) in a 250 mL Schlenk flask and dissolving the starting material by adding 85 mL of dry toluene thereto, 4.4 mL of n-BuLi (2.5 M in n-Hx) was added thereto at −78° C. and the mixture was stirred at room temperature for 5 hrs. The mixture was cooled to −78° C. again and transferred to a Schlenk flask in which 1.7 g of HfCl$_4$ solution (5.2 mmol in 20 mL toluene) of −78° C. was put beforehand by using a cannula, and then it was stirred at room temperature through the night. After the reaction was terminated, the product was filtered with a glass frit (G4) on which celite spread. The remaining solid on the glass frit was washed out thrice with about 3 mL of dry toluene. The toluene solution was vacuum dried and the solid of red color was obtained. The remaining solid on the glass frit was dissolved out by using dichloromethane (DCM). The solid of red color was obtained by vacuum drying the DCM filtrate. As the result of $^1$H-NMR analysis, both of two solids were Hf complex of rac:meso=1:1. After collecting the crude product and storing the same in the oil bath of 45° C., 50 mL of dry toluene was added thereto with stirring for dissolving the same. The solution was stored in a freezer of −30° C. for 3 days for recrystallization. The obtained red solid was filtered with a glass frit (G4) and washed twice with 3 mL of dry n-hexane, and then 1.0 g of the final product (1.2 mmol, 23% yield) of racemic body was obtained by vacuum drying the solid.

$^1$H-NMR (Tol-d$_3$): δ 7.23 (d, J=9.0 Hz, 2H, 7,7'-H in indenyl), 6.98 (d, J=7.5 Hz, 2H, 5,5'-H in quinolinyl), 6.90 (d, J=7.0 Hz, 2H, 5,5'-H in indenyl), 6.82-6.79 (m, 2H, 7,7'-H in quinolinyl), 6.72 (dd, J$_1$=8.5 Hz, J$_2$=7.5 Hz, 2H, 6,6'-H in indenyl), 6.68-6.65 (m, 2H, 6,6'-H in quinolinyl), 6.57 (s, 2H, 3,3'-H in indenyl), 6.51 (d, J=8.5 Hz, 2H, 8,8'-H in quinolinyl), 3.81-3.66 (m, 4H, 2,2'-H in quinolinyl), 2.63-2.53 (m, 4H, 4,4'-H in quinolinyl), 2.03 (s, 6H, 2,2'-Me), 1.87-1.67 (m, 4H, 3,3'-H in quinolinyl), 0.82 (s, 6H, SiMe$_2$)

Comparative Example 1 rac-1,1'-dimethtylsilylene-bis(indenyl) hafnium dichloride rac-1,1'-dimethtylsilylene-bis(indenyl) hafnium dichloride compound was synthesized according to Example 1 disclosed in U.S. Pat. No. 5,905,162.

Preparation of Propylene Homopolymer

Example 3

After putting toluene solvent (200 mL) in a 300 mL miniclave reactor, the temperature of the reactor was preheated to 70° C. 5 mL of 1×10$^{-3}$ M dimethylanilinium tetrakis(pentafluorophenyl) borate cocatalyst and the transition metal compound of Example 1 (5×10$^{-4}$ M, 1 mL) treated with triisobutylaluminum compound were put in the reactor in order. The polymerization reaction was started while continuously injecting propylene (5 bar) therein. After carrying out the reaction for 10 mins, the remaining gas was removed therefrom and the polymer solution was poured to an excess of ethanol in a beaker for inducing the precipitation. The obtained polymer was washed with ethanol and acetone respectively twice or thrice and dried for 12 hrs or more in a vacuum oven of 80° C. And then, the properties of the polymer were measured.

Example 4

The olefin polymer was prepared according to the same method as in Example 3, except that the transition metal compound of Example 2 was used.

Comparative Example 2

The olefin polymer was prepared according to the same method as in Example 3, except that the transition metal compound of Comparative Example 1 was used.

The melting points (Tm) of the polymers were measured by using Q100 of TA Co., Ltd. The values were obtained during the second heating scan of 10° C./min, for eliminating the thermal history of the polymers.

The properties of the polymers of Examples 3 and 4, and Comparative Example 2 were measured by the method, and the results are listed in the following Table 1.

TABLE 1

|  | Catalytic activity (unit: kg/mmol hr) | Weight of polymer (unit: g) | Tm (unit: ° C.) |
| --- | --- | --- | --- |
| Example 3 | 101 | 8.4 | 132.8 |
| Example 4 | 204 | 17.0 | 144.8 |
| Comparative Example 2 | 151 | 12.6 | 122.5 |

Referring to Table 1, the propylene polymers prepared in Examples 3 and 4 show higher melting point (Tm) in comparison to the polymer of Comparative Example 2. Namely, it is recognized that the olefin polymer having high isotacticity is obtained when the transition metal composition of the present invention is used as the catalyst.

Preparation of Ethylene-Propylene Homopolymer

Example 5

After putting toluene solvent (0.8 L) and propylene (100 g) in a 2 L autoclave reactor, the temperature of the reactor was preheated to 70° C. The transition metal compound of Example 1 (5×10$^{-4}$M, 2 mL) treated with triisobutylaluminum compound was put in a catalyst storage tank and subsequently put in the reactor by providing high pressure argon, and 10 mL of 1×10$^{-3}$M dimethylanilinium tetrakis(pentafluorophenyl) borate cocatalyst was put in the reactor by providing high pressure argon successively. The reaction was carried out for 10 mins. The heat of reaction was eliminated through a cooling coil inside the reactor and the polymerization temperature was maintained as uniform as possible. After carrying out the reaction for 10 mins, the remaining gas was removed therefrom, the polymer solution was drained through the bottom of the reactor, and the precipitation was induced by adding an excess of ethanol to the polymer solution and cooling the same. The obtained polymer was washed with ethanol and acetone respectively twice or thrice and dried for 12 hrs or more in a vacuum oven of 80° C. And then, the properties of the polymer were measured.

Comparative Example 3

The olefin polymer was prepared according to the same method as in Example 5, except that the transition metal compound of Comparative Example 1 was used.

For measuring the density, the polymers were made into disc sheets having the thickness of 3 mm and the radius of 2 mm respectively with a press mold of 190° C. and cooled with the speed of 10° C./min, and the weight of the disc was measured by using a Mettler balance. The melt flow rates (MFR) of the polymers were measured by ASTM D-1238 (condition E, 230° C., 2.16 kg load). The melting points (Tm) were measured by using Q100 of TA Co., Ltd. The values were obtained during the second heating scan of 10° C./min, for eliminating the thermal history of the polymers.

The properties of the polymers of Example 5 and Comparative Example 3 were measured by the method, and the results are listed in the following Table 2.

TABLE 2

| | Weight of polymer (unit: g) | Density (unit: g/cc) | MFR (unit: g/10 min) | Tm (unit: ° C.) | Catalytic activity (unit: kg/ mmol hr) |
|---|---|---|---|---|---|
| Example 5 | 87.1 | 0.873 | 15 | 86 | 1045 |
| Comparative Example 3 | 86.6 | 0.856 | 13 | — | 1040 |

What is claimed is:

1. A ligand compound, represented by the following Chemical Formula 1:

[Chemical Formula 1]

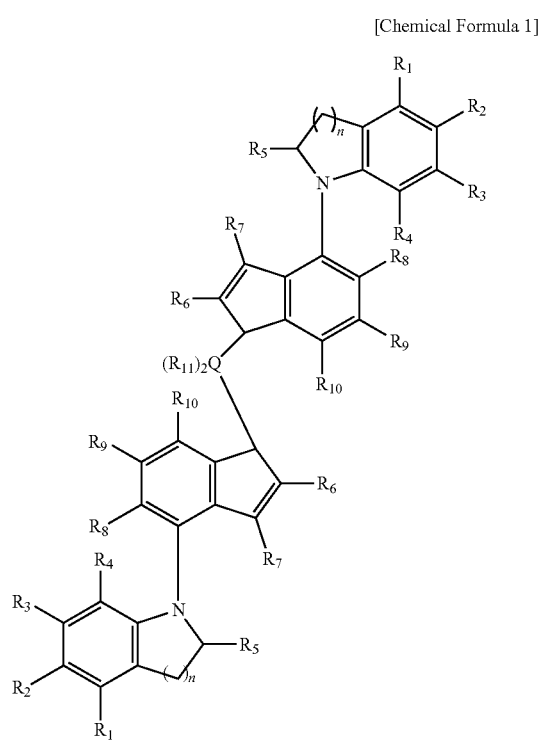

in Chemical Formula 1, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl; and Q is carbon or silicon.

2. The ligand compound according to claim 1, wherein $R_1$ to $R_{10}$ are independently hydrogen or a $C_1$-$C_{20}$ alkyl, and $R_{11}$ is a $C_1$-$C_{20}$ alkyl or a $C_6$-$C_{20}$ aryl in Chemical Formula 1.

3. The ligand compound according to claim 1, wherein the compound represented by Chemical Formula 1 is represented by any one structural formulae serlected from the group consisting of:

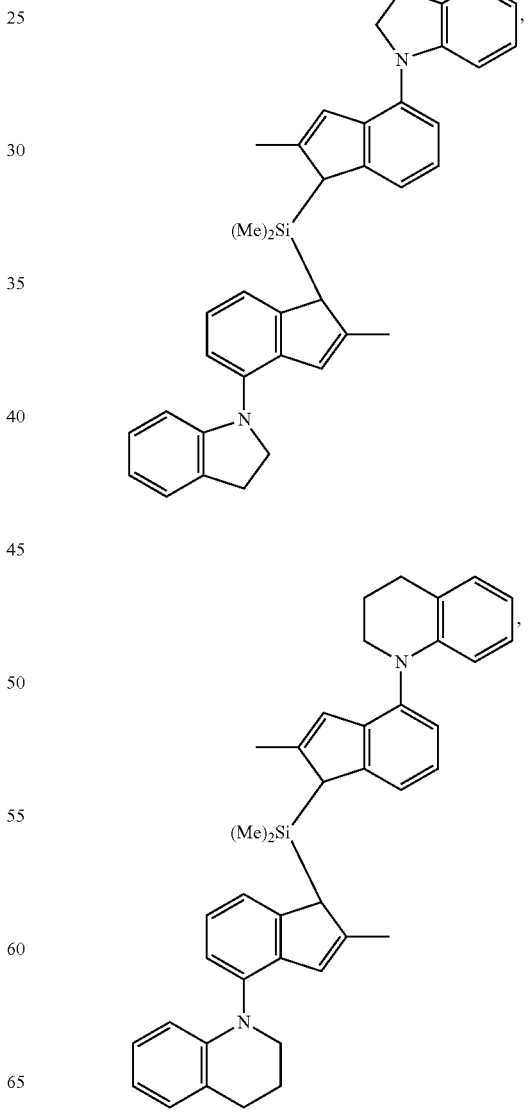

27
-continued
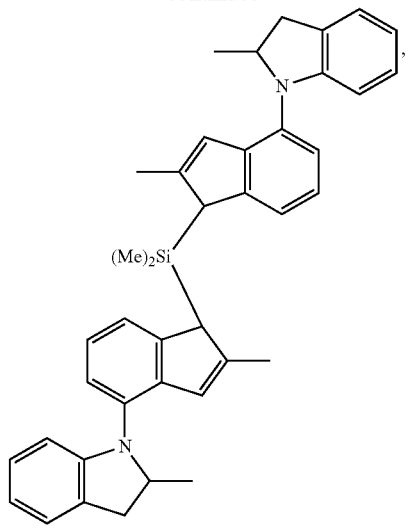
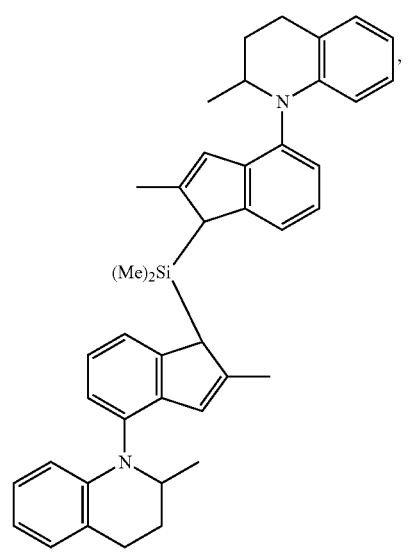
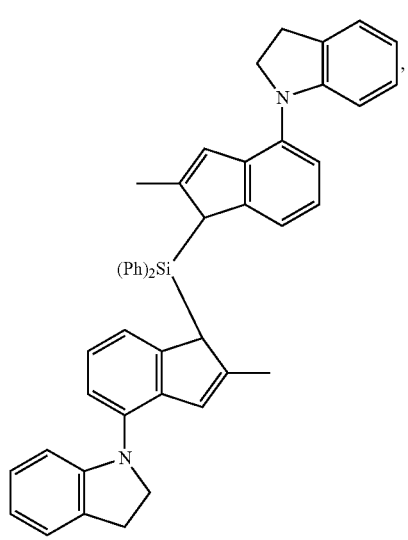
28
-continued
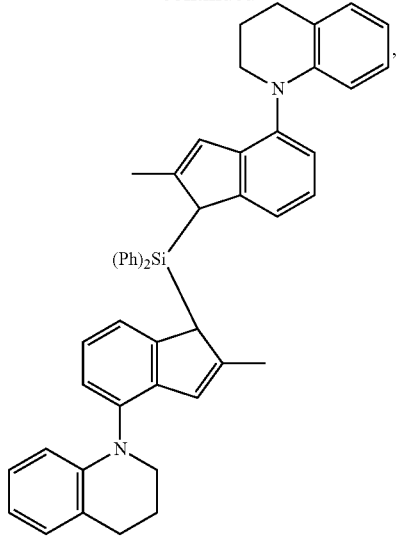
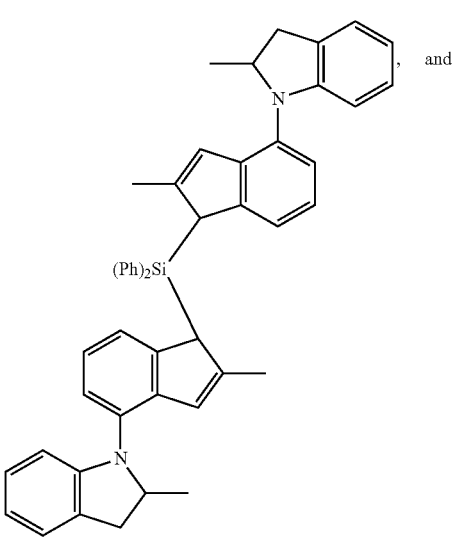, and
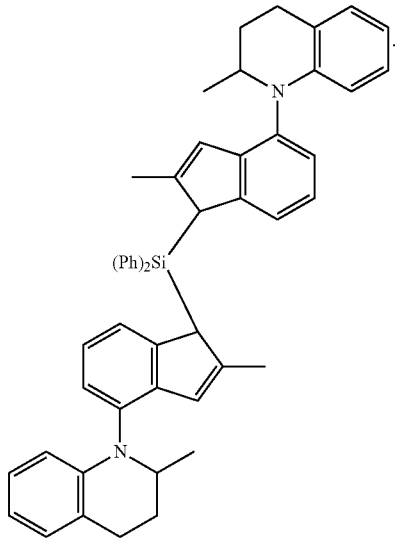

4. A transition metal compound, represented by the following Chemical Formula 2:

[Chemical Formula 2]

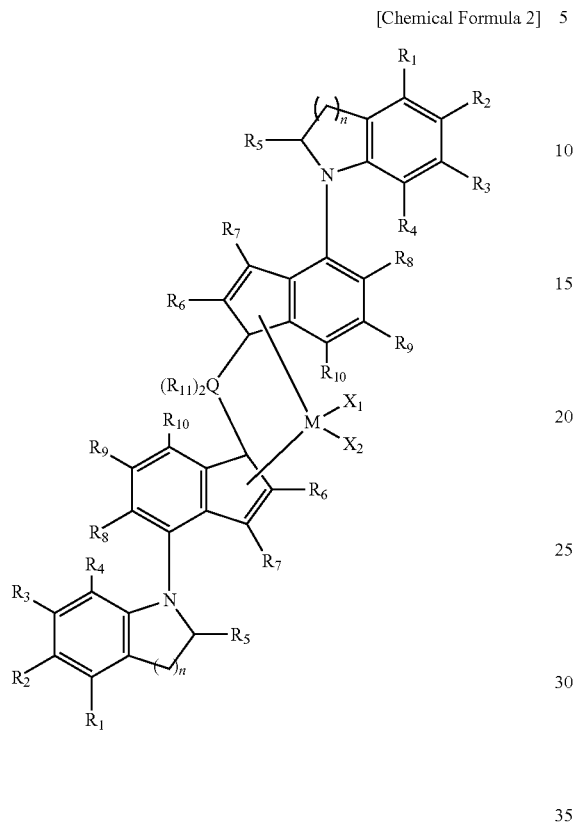

in Chemical Formula 2, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

5. The transition metal compound according to claim 4, wherein $R_1$ to $R_{10}$ are independently hydrogen or a $C_1$-$C_{20}$ alkyl, and $R_{11}$ is a $C_1$-$C_{20}$ alkyl or a $C_6$-$C_{20}$ aryl.

6. The transition metal compound according to claim 4, wherein the M is a metal selected from the group consisting of Ti, Zr, and Hf.

7. The transition metal compound according to claim 4, wherein the transition metal compound represented by Chemical Formula 2 is represented by any one structural formulae selected from the group consisting of:

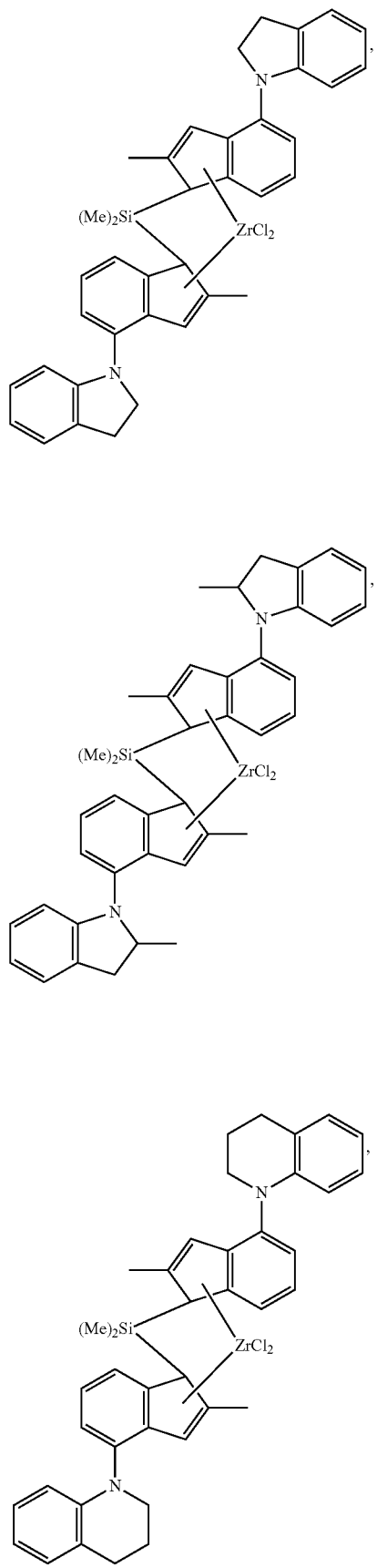

31
-continued
32
-continued
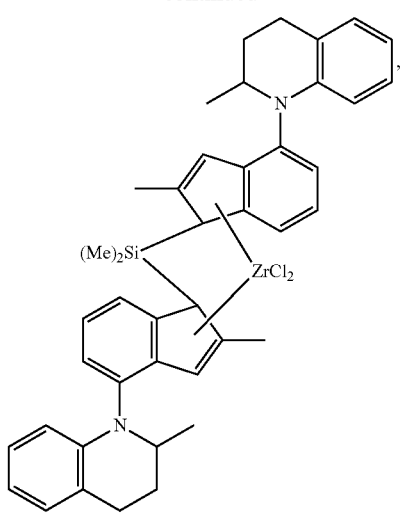
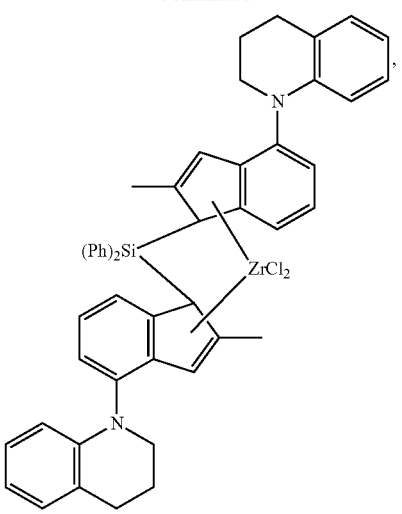

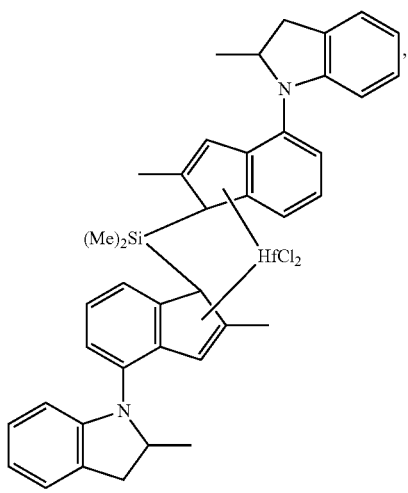
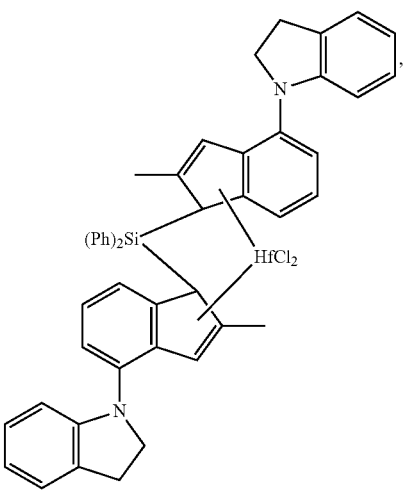
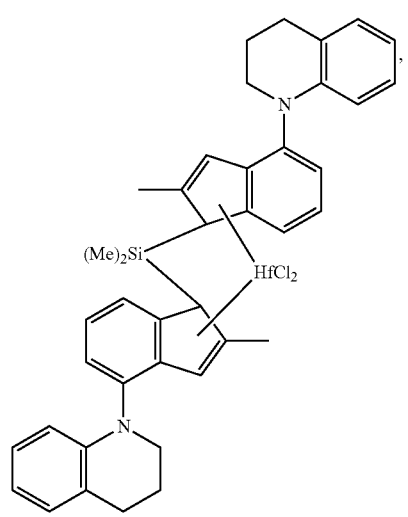
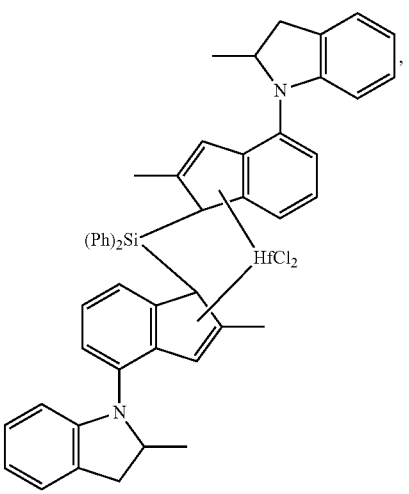

-continued

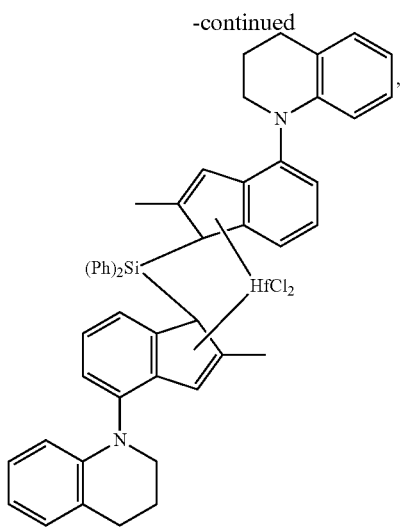

and

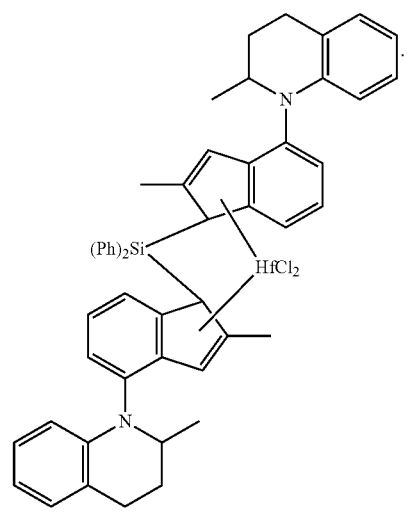

8. A method for preparing ligand compound represented by the following Chemical Formula 1, including the steps of:
carrying out the reaction of the compound represented by the following Chemical Formula 3 and the compound represented by the following Chemical Formula 4 so as to prepare the compound represented by the following Chemical Formula 5; and
carrying out the reaction of the compound represented by the following Chemical Formula 5 or the lithium salt thereof and the compound represented by the following Chemical Formula 6:

[Chemical Formula 3]

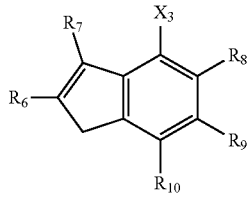

-continued

[Chemical Formula 4]

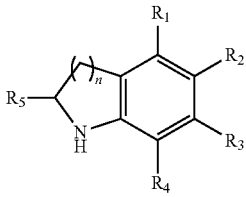

[Chemical Formula 5]

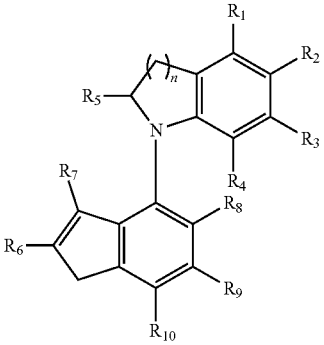

[Chemical Formula 6]

$(R_{11})_2QCl_2$

[Chemical Formula 1]

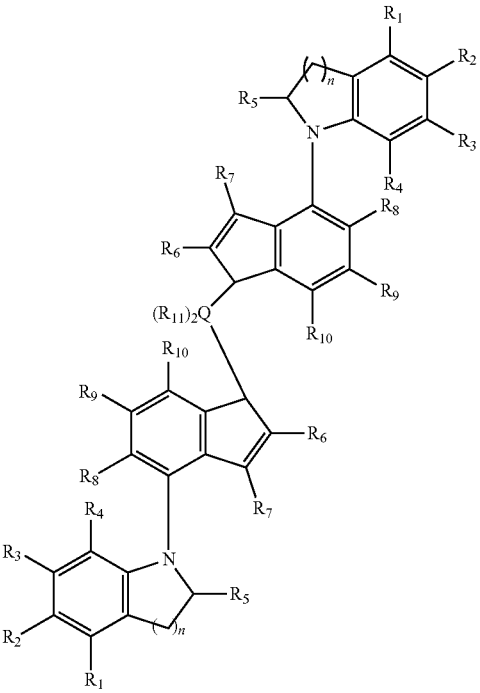

in Chemical Formulae 1, 3, 4, 5, and 6,
n is an integer of 1 to 2;
$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

$X_3$ is a halogen; and

Q is carbon or silicon.

9. The method according to claim 8, wherein $R_1$ to $R_{10}$ are independently hydrogen or a $C_1$-$C_{20}$ alkyl, and $R_{11}$ is a $C_1$-$C_{20}$ alkyl or a $C_6$-$C_{20}$ aryl in Chemical Formula 1.

10. A method for preparing transition metal compound represented by the following Chemical Formula 2, including the step of carrying out the reaction of the ligand compound represented by the following Chemical Formula 1 and the compound represented by the following Chemical Formula 7:

[Chemical Formula 1]

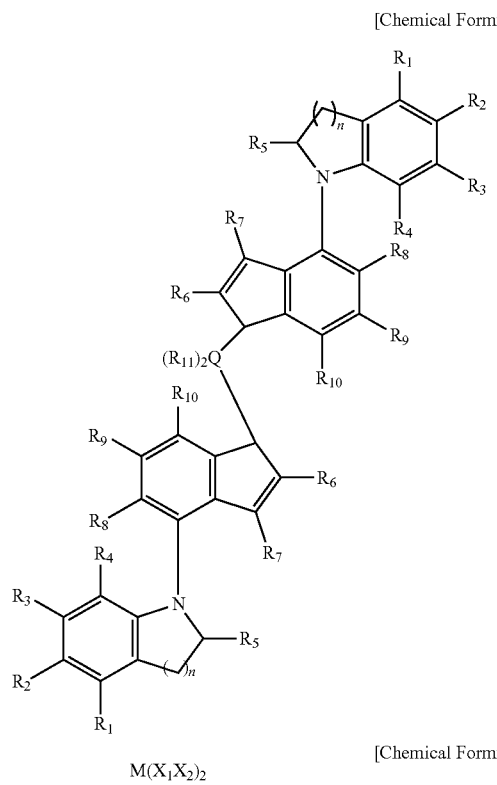

$M(X_1X_2)_2$     [Chemical Formula 7]

-continued

[Chemical Formula 2]

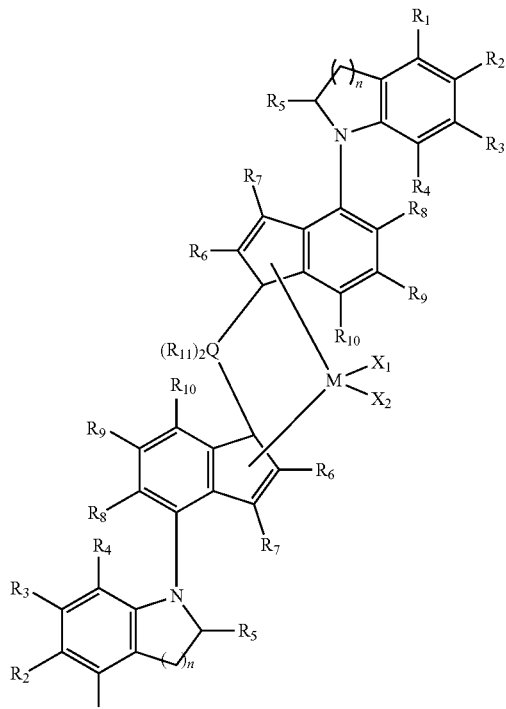

in Chemical Formulae 1, 2, and 7, n is an integer of 1 to 2;

$R_1$ to $R_{10}$ are equal to or different from each other, and are independently hydrogen, a $C_1$-$C_{20}$ alkyl, a $C_1$-$C_{20}$ alkoxy, a $C_2$-$C_{20}$ alkenyl, a $C_6$-$C_{20}$ aryl, a $C_7$-$C_{20}$ alkylaryl, a $C_7$-$C_{20}$ arylalkyl, or silyl, and 2 or more adjacent groups among $R_1$ to $R_{10}$ may be connected together via an alkylidine group including a $C_1$-$C_{20}$ alkyl group or a $C_6$-$C_{20}$ aryl group to form a ring;

$R_{11}$ is hydrogen, a halogen, a $C_1$-$C_{20}$ alkyl, a $C_1$-$C_{20}$ alkoxy, or a $C_6$-$C_{20}$ aryl;

Q is carbon or silicon;

M is a Group 4 transition metal; and $X_1$ and $X_2$ are equal to or different from each other, and are independently a halogen, a $C_1$-$C_{20}$ alkyl, a $C_2$-$C_{20}$ alkenyl, a $C_6$-$C_{20}$ aryl, a $C_7$-$C_{20}$ alkylaryl, a $C_7$-$C_{20}$ arylalkyl, a $C_1$-$C_{20}$ alkylamino, a $C_6$-$C_{20}$ arylamino, or a $C_1$-$C_{20}$ alkylidene group.

11. The method according to claim 10, wherein $R_1$ to $R_{10}$ are independently hydrogen or a $C_1$-$C_{20}$ alkyl, and $R_{11}$ is a $C_1$-$C_{20}$ alkyl or a $C_6$-$C_{20}$ aryl.

12. The method according to claim 10, wherein the M is a metal selected from the group consisting Ti, Zr, and Hf.

\* \* \* \* \*